(12) United States Patent
Kharin et al.

(10) Patent No.: US 10,265,119 B2
(45) Date of Patent: Apr. 23, 2019

(54) ELECTROSURGICAL FORCEPS

(71) Applicant: COVIDIEN LP, Mansfield, MA (US)

(72) Inventors: Nikolay A. Kharin, Loveland, CO (US); Ronald J. Podhajsky, Boulder, CO (US); William Scott Darrow, Longmont, CO (US); Arlen J. Reschke, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 491 days.

(21) Appl. No.: 14/173,391

(22) Filed: Feb. 5, 2014

(65) Prior Publication Data
US 2014/0236149 A1  Aug. 21, 2014

Related U.S. Application Data

(60) Provisional application No. 61/765,177, filed on Feb. 15, 2013.

(51) Int. Cl.
*A61B 17/32* (2006.01)
*A61B 18/00* (2006.01)
*A61B 18/14* (2006.01)

(52) U.S. Cl.
CPC .. *A61B 18/1445* (2013.01); *A61B 17/320092* (2013.01); *A61B 2018/00601* (2013.01); *A61B 2018/00994* (2013.01)

(58) Field of Classification Search
CPC .. A61B 2018/1455; A61B 2018/00994; A61B 17/285; A61B 17/295; A61B 17/320092; A61N 2007/0004
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 14/098,953, filed Dec. 6, 2013; inventor: Cunningham.

(Continued)

*Primary Examiner* — Ronald Hupczey, Jr.

(57) ABSTRACT

An electrosurgical forceps is provided. The electrosurgical forceps includes an end effector including first and second jaw members. One of the first and second jaw members is movable from an open configuration for positioning tissue between the first and second jaw members to a closed configuration for grasping tissue for subsequent electrosurgical treatment thereof. One or more cutting electrodes are positioned on the first and/or second jaw members. The cutting electrode(s) includes one or more piezo-elements that are configured to oscillate at a predetermined frequency when the cutting electrode(s) is energized to sever tissue.

10 Claims, 3 Drawing Sheets

(56) References Cited

U.S. PATENT DOCUMENTS

| | | | |
|---|---|---|---|
| 4,936,281 A * | 6/1990 | Stasz | A61B 5/042 600/439 |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,695,511 A * | 12/1997 | Cano | A61B 17/32002 606/1 |
| 5,728,089 A * | 3/1998 | Lal | A61B 17/320068 601/2 |
| H1745 H | 4/1998 | Paraschac | |
| 5,797,941 A * | 8/1998 | Schulze | A61B 18/1442 606/171 |
| D402,028 S | 12/1998 | Grimm et al. | |
| D408,018 S | 4/1999 | McNaughton | |
| D416,089 S | 11/1999 | Barton et al. | |
| 6,004,335 A * | 12/1999 | Vaitekunas | A61B 17/07207 227/180.1 |
| 6,036,667 A * | 3/2000 | Manna | A61B 17/320092 604/22 |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| 6,340,352 B1 * | 1/2002 | Okada | A61B 17/32009 601/2 |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,115,139 B2 | 10/2006 | McClurken et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,449,004 B2 * | 11/2008 | Yamada | A61B 17/2202 600/104 |
| D582,038 S | 12/2008 | Swoyer et al. | |
| 7,625,370 B2 | 12/2009 | Hart et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,806,892 B2 | 10/2010 | Makin et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,922,651 B2 * | 4/2011 | Yamada | A61B 17/2202 600/104 |
| D649,249 S | 11/2011 | Guerra | |
| D649,643 S | 11/2011 | Allen, IV et al. | |
| D661,394 S | 6/2012 | Romero et al. | |
| 8,192,433 B2 | 6/2012 | Johnson et al. | |
| 8,241,282 B2 | 8/2012 | Unger et al. | |
| D670,808 S | 11/2012 | Moua et al. | |
| 8,333,765 B2 | 12/2012 | Johnson et al. | |
| 8,388,647 B2 | 3/2013 | Nau, Jr. et al. | |
| D680,220 S | 4/2013 | Rachlin | |
| 8,679,115 B2 | 3/2014 | Reschke | |
| 8,685,009 B2 | 4/2014 | Chernov et al. | |
| 8,734,445 B2 | 5/2014 | Johnson et al. | |
| 8,961,547 B2 * | 2/2015 | Dietz | A61B 17/22004 604/22 |
| 8,968,283 B2 * | 3/2015 | Kharin | A61B 17/320092 606/27 |
| 2003/0069571 A1 | 4/2003 | Treat et al. | |
| 2004/0054364 A1 * | 3/2004 | Aranyi | A61B 17/320068 606/27 |
| 2007/0118111 A1 | 5/2007 | Weinberg | |
| 2007/0260242 A1 | 11/2007 | Dycus et al. | |
| 2009/0054886 A1 * | 2/2009 | Yachi | A61B 17/320092 606/27 |
| 2009/0248019 A1 | 10/2009 | Falkenstein et al. | |
| 2010/0185197 A1 * | 7/2010 | Sakao | A61B 18/085 606/51 |
| 2011/0306972 A1 | 12/2011 | Widenhouse et al. | |
| 2012/0059374 A1 | 3/2012 | Johnson et al. | |
| 2012/0095460 A1 * | 4/2012 | Rooks | A61B 17/28 606/45 |
| 2012/0150176 A1 | 6/2012 | Weizman | |
| 2012/0215243 A1 * | 8/2012 | Fujii | A61B 17/2202 606/169 |
| 2012/0296334 A1 * | 11/2012 | Kharin | A61B 17/32009 606/52 |
| 2013/0218185 A1 | 8/2013 | Sanai | |
| 2013/0289561 A1 | 10/2013 | Waaler et al. | |
| 2015/0148804 A1 | 5/2015 | Rooks et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |

(56) References Cited

FOREIGN PATENT DOCUMENTS

| | | |
|---|---|---|
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).

(56) References Cited

OTHER PUBLICATIONS

Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.

* cited by examiner

ELECTROSURGICAL FORCEPS

CROSS REFERENCE TO RELATED APPLICATION

The present application claims the benefit of and priority to U.S. Provisional Application Ser. No. 61/765,177, filed on Feb. 15, 2013, the entire contents of which are incorporated herein by reference.

BACKGROUND

Technical Field

The present disclosure relates to an electrosurgical forceps. More particularly, the present disclosure relates to an electrosurgical forceps that utilizes a combined modality cutting electrode to sever tissue that has been electrosurgically treated.

Description of Related Art

Electrosurgical forceps (e.g., open and closed style forceps) that are configured to electrosurgically treat tissue and, subsequently, sever the treated tissue are well known in the art. For example, both open and closed style forceps may utilize a knife blade or a cutting electrode to sever electrosurgically treated tissue. While such electrosurgical forceps may work well in a number of applications, one or more drawbacks may be associated with these cutting mechanisms. For example, the knife blade may dull over time. Moreover, collateral damage to tissue resulting from thermal spread when the cutting electrode is being utilized to sever electrosurgically treated tissue is sometimes unavoidable.

SUMMARY

As can be appreciated, an electrosurgical forceps that utilizes a combined modality cutting electrode to sever tissue that has been electrosurgically treated may prove useful in the surgical arena.

Embodiments of the present disclosure are described in detail with reference to the drawing figures wherein like reference numerals identify similar or identical elements. As used herein, the term "distal" refers to the portion of a surgical instrument that is being described which is further from a user, while the term "proximal" refers to the portion of the surgical instrument that is being described which is closer to a user.

An aspect of the preset disclosure provides an electrosurgical forceps. The electrosurgical instrument may be an endoscopic electrosurgical forceps or a closed electrosurgical forceps. The electrosurgical forceps includes an end effector including first and second jaw members. One of the first and second jaw members is movable from an open configuration for positioning tissue between the first and second jaw members to a closed configuration for grasping tissue for subsequent electrosurgical treatment thereof. One or more cutting electrodes may be positioned on the first and/or second jaw members. The cutting electrode(s) includes one or more piezo-elements that are configured to oscillate at a predetermined frequency when the cutting electrode(s) is energized to sever tissue.

The piezo-element(s) may be formed from ceramic or crystal. The piezo-element(s) may be mounted within the cutting electrode(s). The piezo-element(s) may be configured to oscillate the cutting electrode(s) at the predetermined frequency along a longitudinal axis defined through the shaft. Alternatively, the piezo-element(s) may be configured to oscillate the cutting electrode(s) at the predetermined frequency transversely relative to a longitudinal axis defined through the shaft.

The piezo-element(s) may be further defined by first and second piezo-elements and the one cutting electrode(s) may be further defined by three or more electrode plates. The first and second piezo-elements may be positioned between the three electrode plates. The first piezo-element may function to oscillate the cutting electrode(s) at the predetermined frequency and the second piezo-element may function to provide feedback to control the first piezo-element.

The first and second jaw members may include respective jaw housings. Each of the jaw housings of the first and second jaw members may include an insulative substrate for supporting an electrode therein. The insulative substrate of the first jaw member may include a longitudinal channel defined therein that is configured to receive the at least one cutting electrode therein. An air gap may be provided between the cutting electrode(s) and a pair of lateral side walls that at least partially define the channel. The air gap facilitates movement of the cutting electrode(s) within the channel when the piezo-element(s) oscillates at the predetermined frequency.

An aspect of the preset disclosure provides an electrosurgical forceps. The electrosurgical instrument may be an endoscopic electrosurgical forceps or a closed electrosurgical forceps. The electrosurgical forceps includes a housing having a shaft extending distally therefrom that defines a longitudinal axis. The electrosurgical forceps includes an end effector including first and second jaw members. One of the first and second jaw members is movable from an open configuration for positioning tissue between the first and second jaw members to a closed configuration for grasping tissue for subsequent electrosurgical treatment thereof. One or more cutting electrodes may be positioned on one or both of the first and second jaw members. The cutting electrode(s) are configured to oscillate at a predetermined frequency and in one or more directions with respect to the longitudinal axis when the cutting electrode(s) is energized to sever tissue.

One or more piezo-element(s) may be provided on the cutting electrode(s). The piezo-element(s) may be formed from ceramic or crystal. The piezo-element(s) may be configured to oscillate the cutting electrode(s) at the predetermined frequency along a longitudinal axis defined through the shaft. Alternatively, the piezo-element(s) may be configured to oscillate the cutting electrode(s) at the predetermined frequency transversely relative to a longitudinal axis defined through the shaft.

The first and second jaw members may include respective jaw housings. Each of the jaw housings of the first and second jaw members may include an insulative substrate for supporting an electrode therein. The insulative substrate of the first jaw member may include a longitudinal channel defined therein that is configured to receive the at least one cutting electrode therein. An air gap may be provided between the cutting electrode(s) and a pair of lateral side walls that at least partially define the channel. The air gap facilitates movement of the cutting electrode(s) within the channel when the piezo-element(s) oscillates at the predetermined frequency.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
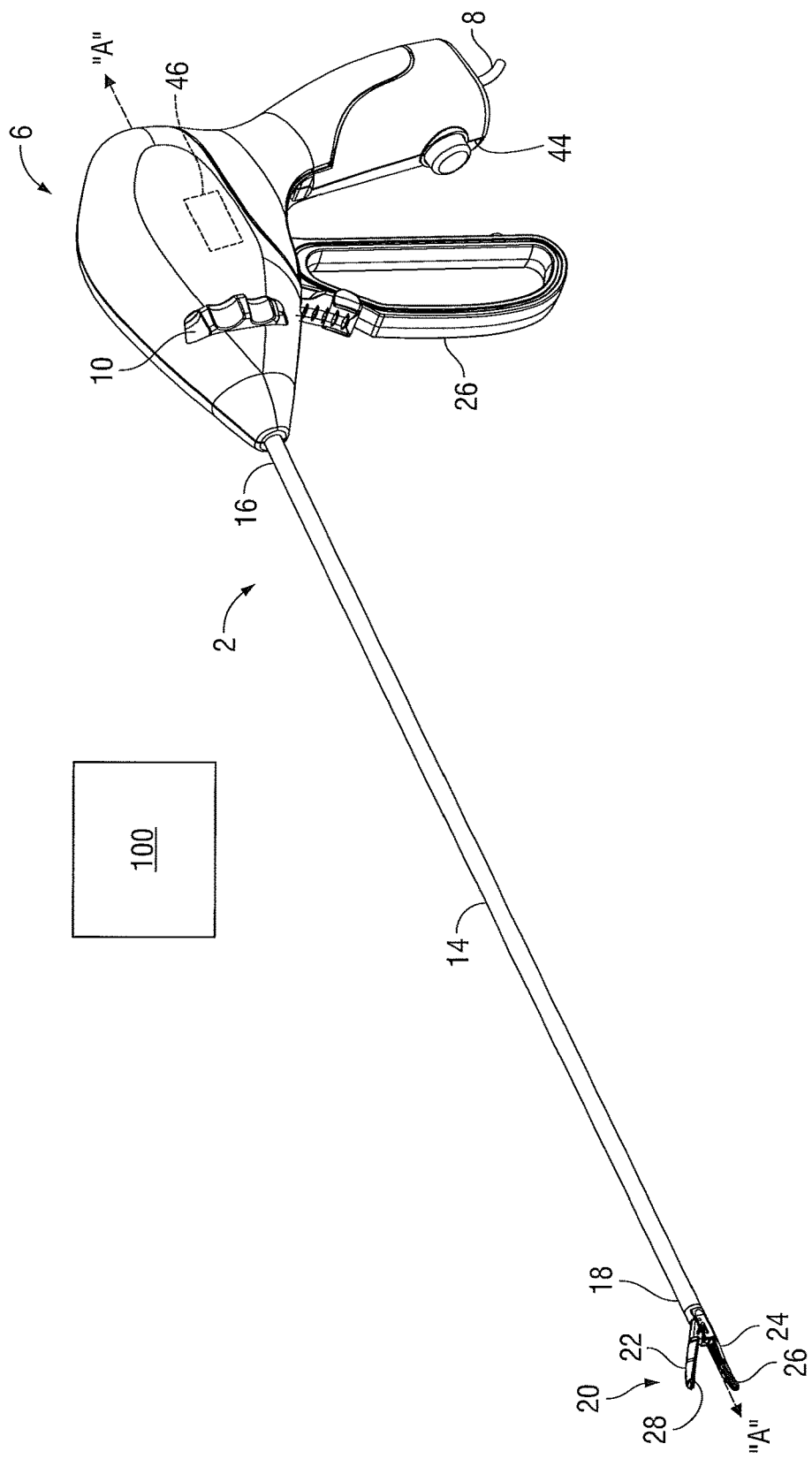
FIG. 1 is a left, perspective view of an endoscopic electrosurgical forceps that utilizes a combined modality cutting electrode according to an embodiment of the present disclosure.
Figure 2:
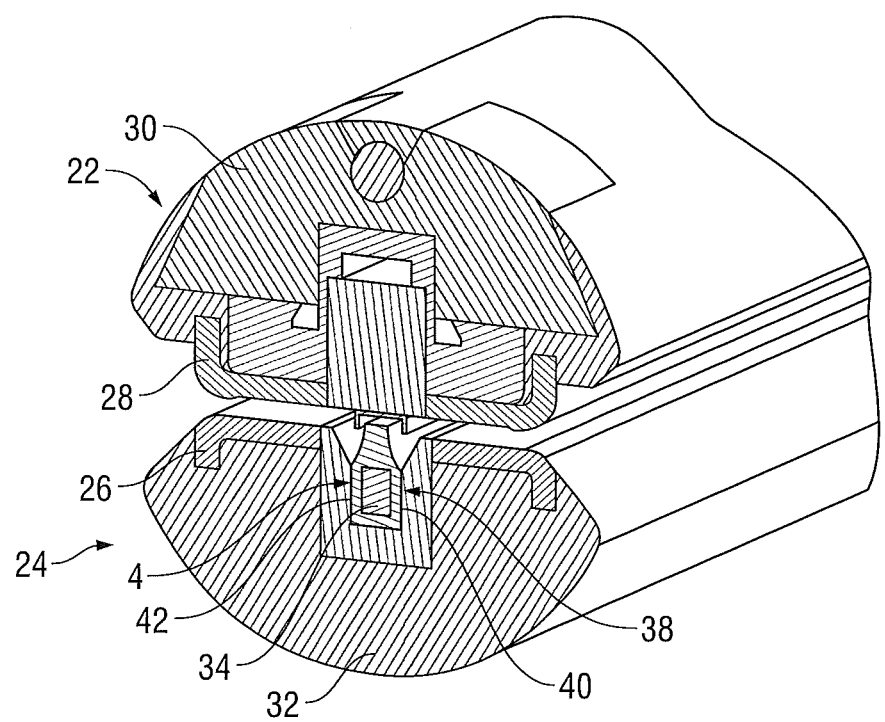
FIG. 2 is a cut-away view of first and second jaw members of the endoscopic electrosurgical forceps.

Turning now to FIG. 1, an electrosurgical forceps, e.g., an endoscopic electrosurgical forceps 2 (forceps 2), that utilizes a combined modality cutting electrode 4 (FIGS. 2-3) according to an embodiment of the present disclosure is shown. Briefly, forceps 2 includes a housing 6 (FIG. 1) that may be formed form one or more suitable materials including, but not limited to plastic, metal, ceramic, etc. Housing 6 is configured to house one or more components, e.g, a cable 8 and/or rotating assembly 10, associated with forceps 2 (FIG. 1). One or more leads (not explicitly shown) that are provided within cable 8 may extend from housing 6 and through a shaft 14 and provide electrosurgical energy, e.g., RF energy and ultrasonic energy, from a generator 100 (FIG. 1) to one or more components of forceps 2, e.g. cutting electrode 4 (FIG. 2). Rotating assembly 8 is configured to rotate shaft 14 about a longitudinal axis "A-A" that is defined through shaft 14.

Continuing with reference to FIG. 1, shaft 14 extends distally from housing 6 and includes proximal and distal ends 16 and 18, respectively. Proximal end 16 operably couples to housing 6 and distal end 18 supports an end effector 20 including first and second jaw members 22, 24 such that rotation of shaft 14 also rotates first and second jaw members 22, 24 about longitudinal axis "A-A."

Jaw members 22, 24 are configured to grasp and, subsequently, electrosurgically treat tissue. Specifically, forceps 2 in this embodiment utilizes a unilateral jaw configuration in which first jaw member 22 is movable with respect to second jaw member 24. In accordance with the instant disclosure, shaft 14 is configured to move first jaw member 22 from an open configuration for positioning target tissue between first and second jaw members 22, 24 to a closed configuration for grasping and, subsequently, electrosurgically treating tissue. More particularly, when a movable handle 26 (FIG. 1) is moved proximally shaft 14 moves distally, which, in turn, moves first jaw member 22 from the open configuration to the closed configuration. Alternatively, forceps 2 may be configured to utilize a bilateral jaw configuration. In this instance, both first and second jaw members 22, 24 may be configured to move with respect to one another for grasping and, subsequently, electrosurgically treating tissue.

Referring to FIG. 2, each of first and second jaw members 22, 24 is configured to electrosurgically treat tissue when electrosurgical energy is transmitted to respective electrodes 28, 26 that are coupled to first and second jaw members 22, 24. Electrodes 28, 26 may be coupled to first and second jaw members 22, 24 via any suitable coupling methods. In the illustrated embodiment, electrodes 28, 26 are secured within respective insulative substrates that form jaw housings 30, 32. In embodiments, an overmolding process may be utilized to form jaw housings 30, 32 with respective electrodes 28, 26 secured thereto. One or more stop members may be provided on electrodes 26, 28 and may be configured to provide a specific gap distance between electrodes 26, 28 when first and second jaw members 22, 24 are in the closed configuration.

Figure 3:
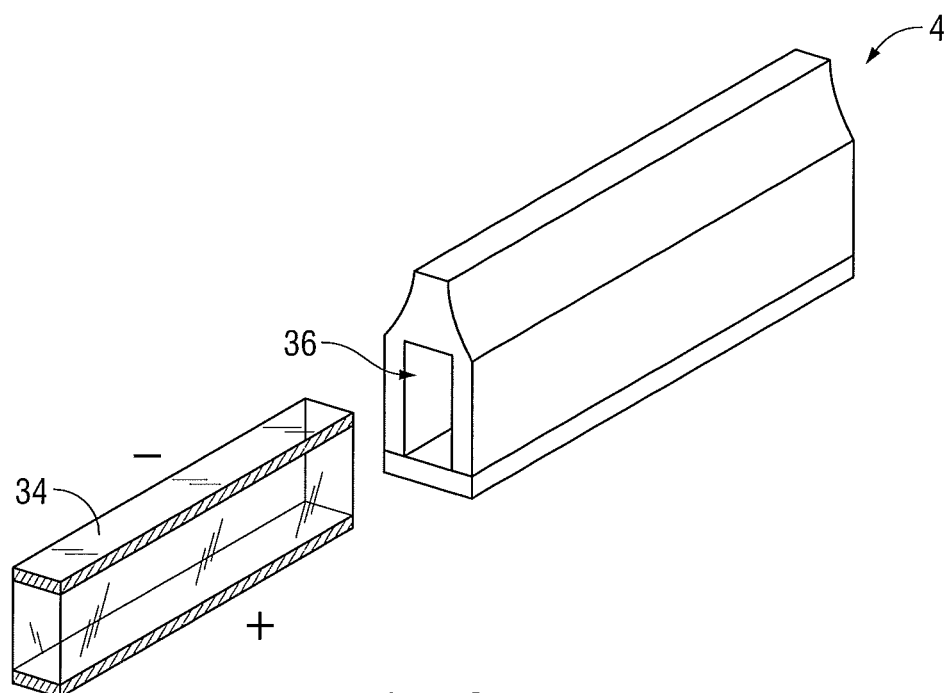
FIG. 3 is a left, perspective with the parts of the combined modality cutting electrode separated.

With reference to FIGS. 2-3, cutting electrode 4 is illustrated. Cutting electrode 4 may be provided on one or both jaw members 22, 24. For illustrative purposes, cutting electrode 4 is shown provided on second jaw member 24. Unlike electrodes 26, 28 which are configured to electrosurgically treat target tissue, cutting electrode 4 is configured to sever electrosurgically treated tissue. Specifically, cutting electrode 4 is configured to oscillate at a predetermined frequency and in one or more directions with respect to longitudinal axis "A-A" (e.g., along longitudinal axis "A-A" and/or transversely relative thereto) when cutting electrode 4 is actively conducting electrosurgical energy to sever tissue that has been electrosurgically treated. With this purpose in mind, one or more piezo-elements 34 (FIGS. 2-3) may be operably coupled to cutting electrode 4.

Piezo-elements 34 may be formed from any suitable material including but not limited to ceramic or crystal. Other suitable materials may also be utilized to form piezo-element 34. In the embodiment illustrated in FIGS. 1-3, piezo-element 34 is securely coupled within a cavity 36 having a configuration that complements piezo-element 34 (as best seen in FIG. 3); this facilitates transferring the motion of piezo-element 34 across the entire cutting electrode 34. One or more suitable coupling methods, e.g., curable adhesive, may be utilized to couple piezo-element 34 within the confines of cavity 36.

Referring again to FIG. 3, a longitudinal channel 38 is defined within the insulative substrate that forms jaw housing 32 and is configured to receive cutting electrode therein such that cutting electrode 4 may move along longitudinal axis "A-A" and/or transversely relative thereto. In accordance with the instant disclosure, an air gap is provided between cutting electrode 34 and a pair of lateral side walls 40, 42 that at least partially defines channel 38. The air gap facilitates movement of cutting electrode 34 within channel 38 when piezo-element 34 oscillates at the predetermined frequency. Moreover, one or more lubricious materials, e.g., polytetrafluoroethylene, may be utilized to coat lateral walls 40, 42 to further facilitate movement of cutting electrode 34 within channel 38 when piezo-element 34 oscillates at the predetermined frequency.

Figure 4:
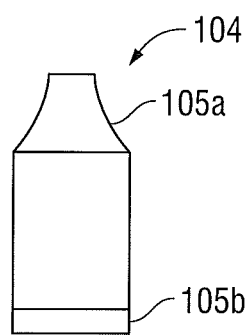
FIG. 4 is a cross-sectional view of a combined modality cutting electrode according to another embodiment of the present disclosure.

With reference now to FIG. 4, a cutting electrode 104 according to an alternate embodiment is illustrated. Unlike cutting electrode 4 that is configured to house piezo-element 34, cutting electrode 104 utilizes a stand-alone piezo-element 134, e.g., a crystal. In the embodiment illustrated in FIG. 4 a pair of electrodes 105a, 105b are electroplated to respective top and bottom surfaces of piezo-element 134.

Other than the specific configuration of cutting electrode 104, cutting electrode 104 functions identically to cutting electrode 4.

With reference again to FIG. 1, a handle assembly 48 includes movable handle 26 and fixed handle 50. Movable handle 26 is movable along the longitudinal axis "A-A" to effectuate movement of first jaw member 22 and fixed handle 50 may be utilized by a clinician to grasp forceps 2. Fixed handle 50 also supports a switch 44 that is configured to supply electrosurgical energy, e.g., RF energy, to electrodes 28, 26 of the first and second jaw member 22, 24.

Continuing with reference to FIG. 1, a trigger assembly 12 is provided on housing 6 and is configured to activate a switch 46 (shown in phantom) disposed within housing 6. Switch 46 communicates with generator 100 and when actuated causes electrical energy to be provided to piezo-element 34 (or piezo-element 134) to stimulate piezo-element 34 and RF energy to be provided to cutting electrode 4.

In use, tissue may be positioned between first and second jaw members 22, 24 and movable handle 26 may be moved proximally to move first jaw member 22 to the closed configuration. Continued movement of movable handle 26 in the proximal direction causes movable handle 26 to engage switch 44, which, in turn, causes RF energy to flow to electrodes 26, 28 to electrosurgically treat, e.g., coagulate, seal, desiccate, etc., tissue Thereafter, a trigger assembly 12 may be depressed, which, in turn, provides RF energy that ranges from about 400 KHz to about 454 KHz to cutting electrode 4. Additionally, electrical energy is provided to piezo-element 34 (or piezo-element 134) which, in turn, electrically stimulates piezo-element 34 (or piezo-element 134) to oscillate at the predetermined frequency that may range from about 1.25 MHz to about 1.5 MHz.

From the foregoing and with reference to the various figure drawings, those skilled in the art will appreciate that certain modifications can also be made to the present disclosure without departing from the scope of the same. For example, in certain embodiments it may prove useful to provide cutting electrode 4 with two piezo-elements 34.

Figure 5:
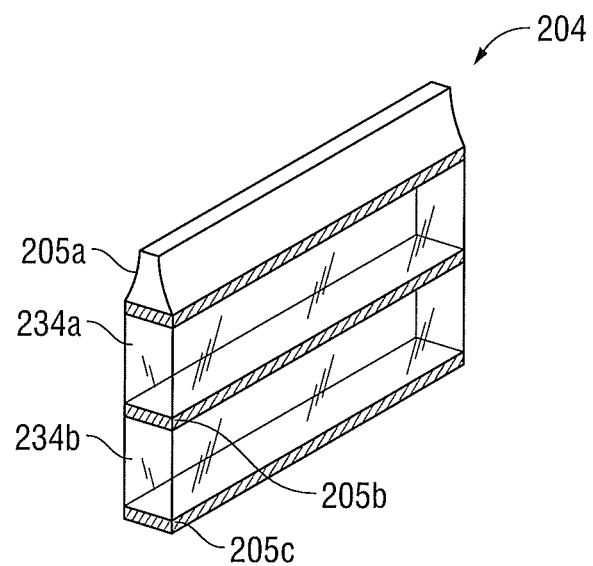
FIG. 5 is a left, perspective view of a combined modality cutting electrode according to yet another embodiment of the present disclosure.

With reference to FIG. 5 a cutting electrode 204 including two piezo-elements 234a, 234b is illustrated. Cutting electrode 204 is substantially similar to cutting electrodes 4, 104. Accordingly, and unless otherwise noted, only the features that are unique to cutting electrode 204 are described in further detail.

Cutting electrode 204 includes three plated electrodes 205a, 205b and 205c that are configured to sever tissue that has been electrosurgically treated. Piezo-elements 234a, 234b are positioned between electrodes 205a-205c and coupled thereto via one or more suitable coupling methods. In an assembled configuration, cutting electrode 204 includes a generally rectangular configuration and may be positioned on one of first and second jaw members 22, 24 (e.g., second jaw member 24) and within longitudinal channel 38 in a manner as described above.

Piezo-elements 234a, 234b may be made from any of the aforementioned materials, e.g., crystal, ceramic, etc., that form piezo-elements 34, 134. In the embodiment illustrated in FIG. 5, piezo-element 234a is utilized as a drive element that functions to oscillate cutting electrode 204 at the predetermined frequency. Piezo-element 234b is utilized as a feedback element that provides feedback to generator 100 (or one or more modules associated therewith) to control oscillation of piezo-element 234a and/or cutting electrode 204.

Operation of forceps 2 with cutting electrode 204 including piezo-elements 234a, 234b is substantially similar to operation of forceps 2 with cutting electrode 4 including piezo-elements 34, 134. Unlike the latter arrangement, however, feedback information pertaining to a surgical procedure may be provided in real-time to generator 100 (or module(s) associated therewith). Feedback information may include, but is not limited to oscillation frequency of cutting electrode 204 and/or piezo-element 234a; temperature of piezo-elements 234a, 234b, cutting electrode 204, target tissue; and one or more electrical parameters that may be present at the surgical site.

Figure 6:
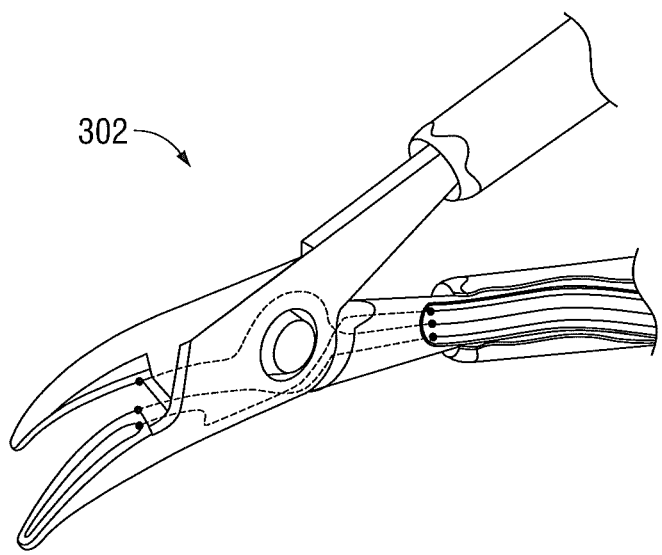
FIG. 6 is a partial, left perspective view of an open style electrosurgical forceps that may be configured for use with the combined modality cutting electrode.

While the aforementioned cutting electrodes 4, 104, 204 including respective piezo-elements 34, 134 and 234a, 234b have been described herein as being utilized with an endoscopic forceps 2, it is within the purview of the instant disclosure that the other types of forceps may also be configured for use with cutting electrodes 4, 104, 204 including respective piezo-elements 34, 134 and 234a, 234b. For example, an open forceps 302 such as the one illustrated in FIG. 6 may be configured for use with cutting electrodes 4, 104, 204 including respective piezo-elements 34, 134 and 234a, 234b. As can be appreciated, one or more modifications may need to be made to cutting electrodes 4, 104, 204 including respective piezo-elements 34, 134 and 234a, 234b in order for forceps 302 to function in a manner as described with respect to forceps 2, 102.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   a housing having a shaft extending distally therefrom and defining a longitudinal axis therethrough;
   an end effector including first and second jaw members, the first and second jaw members having a first and a second jaw housing, respectively, wherein each of the first and second jaw housings of the first and second jaw members includes an insulative substrate for respectively supporting a first and a second electrode therein, the insulative substrate of each of the first and second jaw housings extending along at least a portion of the respective first and second electrodes, at least one of the first or second jaw members defining a longitudinal channel between a pair of lateral side walls that are disposed on opposite sides of a central longitudinal axis defined by the longitudinal channel, at least one of the first or second jaw members movable from an open configuration for positioning tissue between the first and second jaw members to a closed configuration for grasping tissue for subsequent electrosurgical treatment thereof;
   at least one cutting electrode defining a longitudinally-extending bore therethrough that extends a majority of an entire length of the at least one cutting electrode, the at least one cutting electrode positioned between the pair of lateral side walls of the longitudinal channel of at least one of the first or second jaw members, such that an air gap is defined transversely between a pair of lateral portions of the at least one cutting electrode and the pair of lateral side walls, respectively, wherein the at least one cutting electrode is configured to oscillate at a predetermined frequency and in at least one direction with respect to the longitudinal axis when the at least one cutting electrode is energized to sever tissue and wherein the air gap is configured to facilitate movement of the at least one cutting electrode within the longitudinal channel; and at least one piezo-element disposed within the bore defined in the at least one cutting electrode.

2. An electrosurgical forceps according to claim 1, wherein the at least one piezo-element is formed from material selected from the group consisting of ceramic and crystal.

3. An electrosurgical forceps according to claim 1, wherein the at least one piezo-element is configured to oscillate the at least one cutting electrode at the predetermined frequency along the longitudinal axis defined through the shaft.

4. An electrosurgical forceps according to claim 1, wherein the at least one piezo-element is configured to oscillate the at least one cutting electrode at the predetermined frequency transversely relative to the longitudinal axis defined through the shaft.

5. An electrosurgical forceps according to claim 1, wherein the insulative substrate of the first jaw member includes the longitudinal channel defined therein that is configured to receive the at least one cutting electrode therein.

6. An electrosurgical forceps according to claim 5, wherein the air gap is configured to facilitate movement of the at least one cutting electrode within the longitudinal channel when the at least one piezo-element oscillates at the predetermined frequency.

7. An electrosurgical forceps according to claim 1, wherein the at least one cutting electrode includes a tissue contacting surface that is accessible through the longitudinal channel to engage tissue.

8. An electrosurgical forceps according to claim 1, wherein the bore extends longitudinally along the length of the at least one cutting electrode from a proximal end of the at least one cutting electrode to a distal end of the at least one cutting electrode.

9. An electrosurgical forceps according to claim 1, wherein the bore has a linear configuration.

10. An electrosurgical forceps according to claim 1, wherein the bore is surrounded by opposing upper and lower inner surfaces of the at least one cutting electrode and opposing lateral inner surfaces of the at least one cutting electrode.

* * * * *